(12) United States Patent
Litterst et al.

(10) Patent No.: US 9,347,094 B2
(45) Date of Patent: May 24, 2016

(54) DIGITAL ASSAY FOR TELOMERE LENGTH

(71) Applicant: Bio-Rad Laboratories, Inc., Hercules, CA (US)

(72) Inventors: Claudia Litterst, Walnut Creek, CA (US); Luis A. Ugozzoli, San Rafael, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 217 days.

(21) Appl. No.: 14/171,393

(22) Filed: Feb. 3, 2014

(65) Prior Publication Data

US 2014/0220569 A1     Aug. 7, 2014

Related U.S. Application Data

(60) Provisional application No. 61/759,768, filed on Feb. 1, 2013.

(51) Int. Cl.
*C12Q 1/68* (2006.01)

(52) U.S. Cl.
CPC ............ *C12Q 1/6858* (2013.01); *C12Q 1/6844* (2013.01)

(58) Field of Classification Search
CPC ........................................................ C12Q 1/68
USPC ....................................................... 436/6.11
See application file for complete search history.

(56) References Cited

U.S. PATENT DOCUMENTS

| | | | |
|---|---|---|---|
| 7,041,481 | B2 | 5/2006 | Anderson et al. |
| 8,535,889 | B2 | 9/2013 | Larson et al. |
| 2010/0173394 | A1 | 7/2010 | Coston, Jr. et al. |
| 2011/0159499 | A1 | 6/2011 | Hindson et al. |
| 2011/0244455 | A1 | 10/2011 | Larson et al. |
| 2011/0250597 | A1* | 10/2011 | Larson et al. ........... 435/6.11 |
| 2012/0070842 | A1 | 3/2012 | Harley et al. |

FOREIGN PATENT DOCUMENTS

| | | | | |
|---|---|---|---|---|
| EP | 2474822 | A1 | 7/2012 | |
| WO | WO2010141385 | * | 12/2010 | ............ G01N 33/48 |
| WO | 2014031908 | A1 | 2/2014 | |
| WO | 2014062726 | A1 | 4/2014 | |

OTHER PUBLICATIONS

Kim NW, Piatyszek MA, Prowse KR, Harley CB, West MD, Ho PL, Coviello GM, Wright WE, Weinrich SL, Shay JW. Specific association of human telomerase activity with immortal cells and cancer. Science. Dec. 23, 1994; 266(5193):2011-5.*
Cawthon RM. Telomere measurement by quantitative PCR. Nucleic Acids Res. May 15, 2002; 30(10):e47.*
Gil ME, Coetzer TL. Real-time quantitative PCR of telomere length. Mol Biotechnol. Jun. 2004;27(2):169-72.*
O'Callaghan N, Dhillon V, Thomas P, Fenech M. A quantitative real-time PCR method for absolute telomere length. Biotechniques. May 2008; 44(6):807-9.*
Zhou X, Xing D. Assays for human telomerase activity: progress and prospects. Chem Soc Rev. Jul. 7, 2012; 41(13):4643-56. Epub May 1, 2012. Review.*
Dressman D, Yan H, Traverso G, Kinzler KW, Vogelstein B. Transforming single DNA molecules into fluorescent magnetic particles for detection and enumeration of genetic variations. Proc Natl Acad Sci U S A. Jul. 22, 2003; 100(15):8817-22. Epub Jul. 11, 2003.*
Vogelstein B, Kinzler KW. Digital PCR. Proc Natl Acad Sci U S A. Aug. 3, 1999; 96(16):9236-41.*
Mieczyslaw A. Piatyszek et al., Detection of telomerase activity in human cells and tumors by a telomeric repeat amplification protocol (TRAP), Methods in Cell Science, vol. 17, 1995, pp. 1-15.
Anthon P. Shuber et al., "A Simplified Procedure for Developing Multiplex PCRs", Genome Research, Nov. 17, 1995, pp. 488-493.
Ariel A. Avilion et al., "Human Telomerase RNA and Telomerase Activity in Immortal Cell Lines and Tumor Tissues", Cancer Research, vol. 56, Feb. 1, 1996, pp. 645-650.
Katarzyna Heller-Uszynska et al., "Microarray TRAP—a high-throughput assay to quantitate telomerase activity", Biochemical and Biophysical Research Communications, vol. 323, May 26, 2004, pp. 465-472.
Richard M. Cawthon, "Telomere length measurement by a novel monochrome multiplex quantitative PCR method", Nucleic Acids Research, vol. 37, No. 3, Feb. 2009, 7 pages.
Jeremy D. Henson et al., "DNA C-circles are specific and quantifiable markers of alternative-lengthening-of-telomeres activity", Nature Biotechnology, vol. 27, No. 12, Dec. 2009, pp. 1181-1186.
Blaine R. Copenheaver, Authorized Officer, International Searching Authority, U.S. Patent and Trademark Office, "International Search Report" in connection with related PCT Patent Application No. PCT/US2014/014461, dated Apr. 23, 2014, 4 pages.
Blaine R. Copenheaver, Authorized Officer, International Searching Authority, U.S. Patent and Trademark Office, "Written Opinion of the International Searching Authority" in connection with related PCT Patent Application No. PCT/US2014/014461, dated Apr. 23, 2014, 10 pages.

* cited by examiner

*Primary Examiner* — Angela M Bertagna
*Assistant Examiner* — Olayinka Oyeyemi
(74) *Attorney, Agent, or Firm* — Kolisch Hartwell, P.C.

(57) ABSTRACT

A method of characterizing telomere length. A template may be synthesized in a bulk phase reaction mixture containing genomic DNA. Partitions may be formed after synthesizing the template in the bulk phase reaction mixture, with only a subset of the partitions containing at least one copy of the template. At least a region of the template may be amplified in partitions. Amplification data may be collected from partitions. A measure of telomere length may be determined for the genomic DNA based on the amplification data. In some embodiments, the bulk phase reaction mixture may be thermally cycled for at least two cycles, and heated to a denaturation temperature and cooled to an annealing temperature in each cycle.

15 Claims, 5 Drawing Sheets

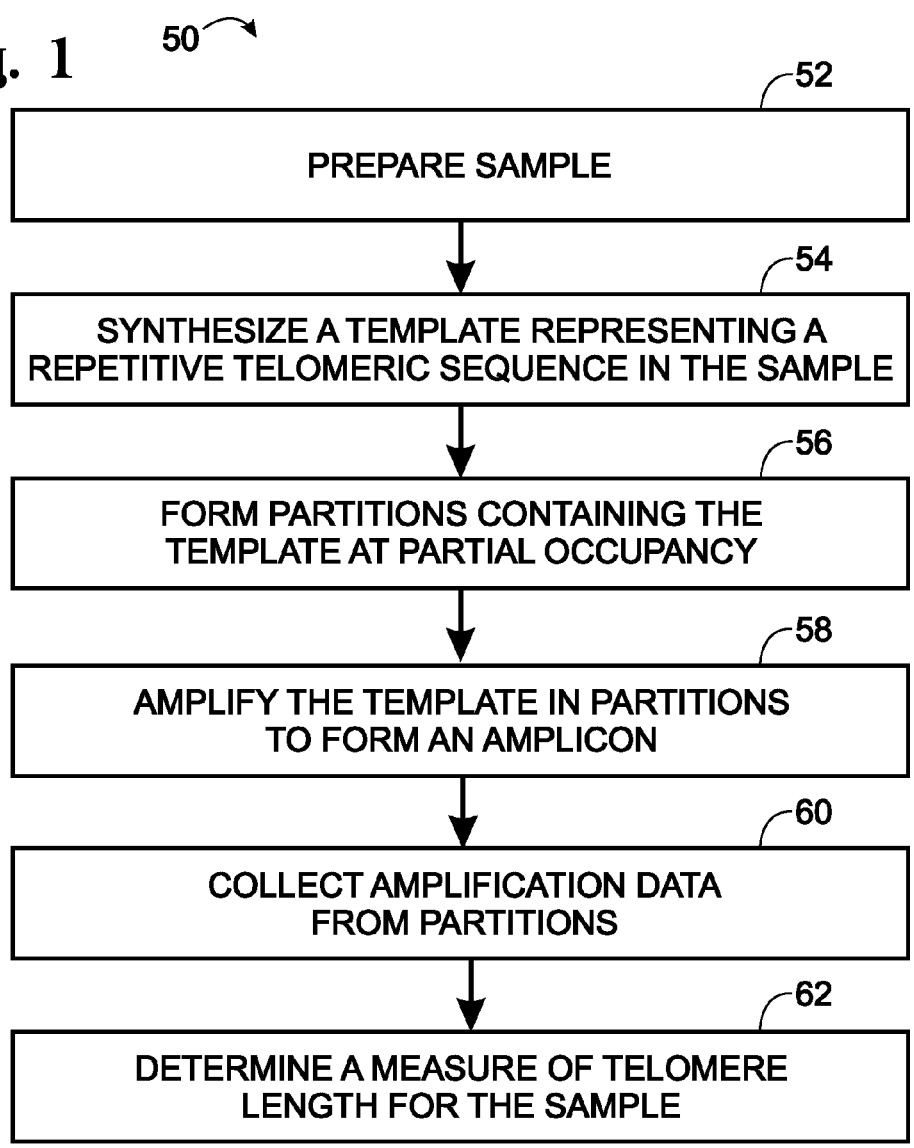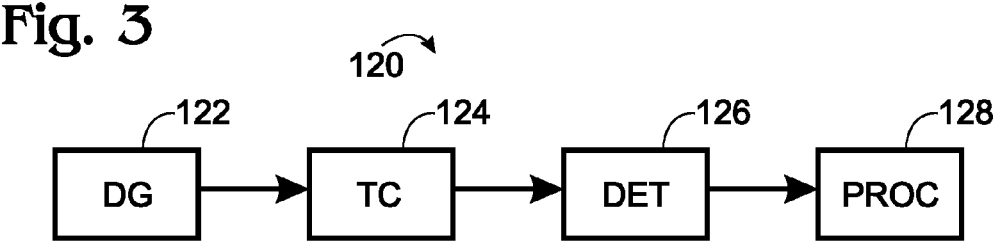

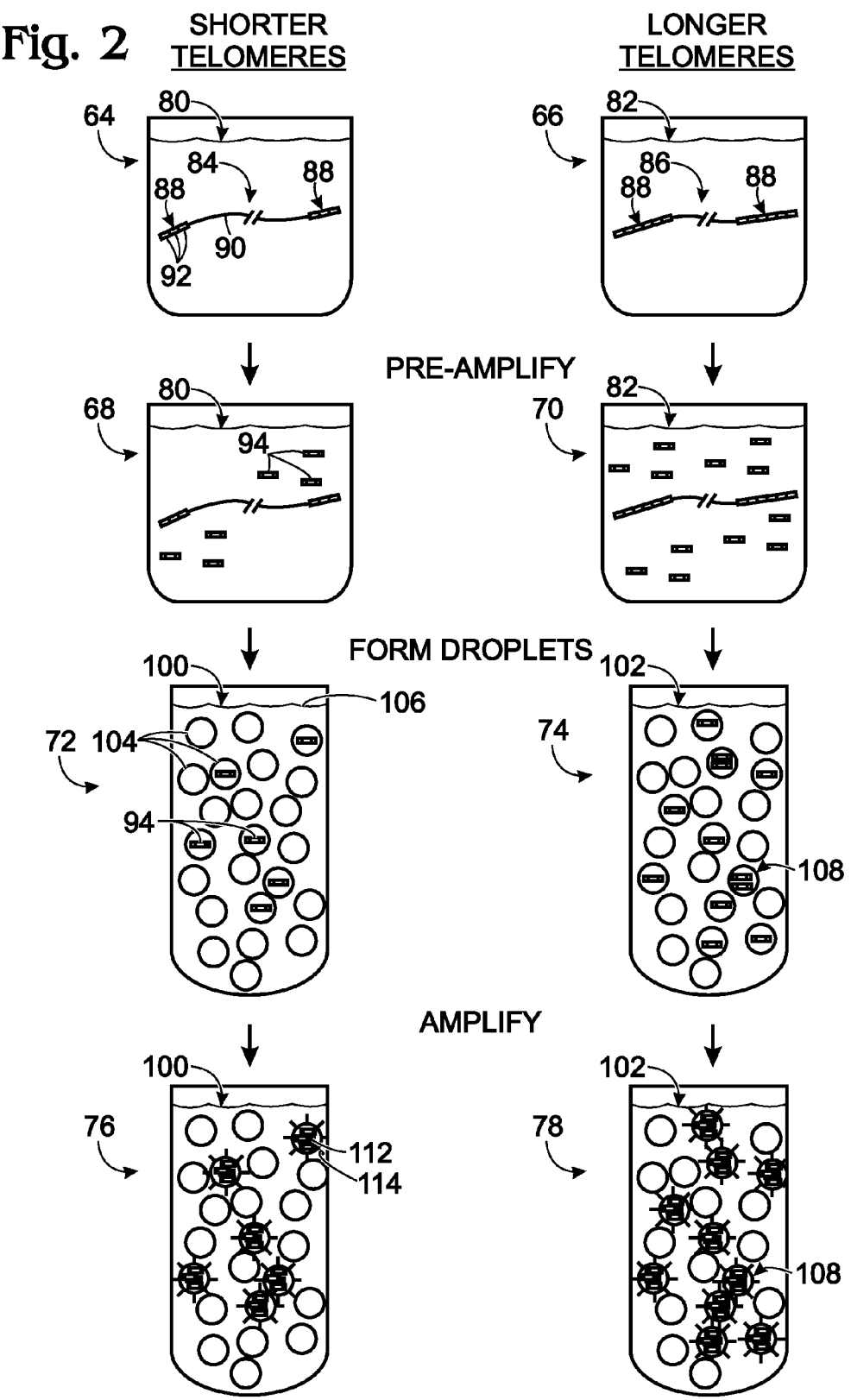

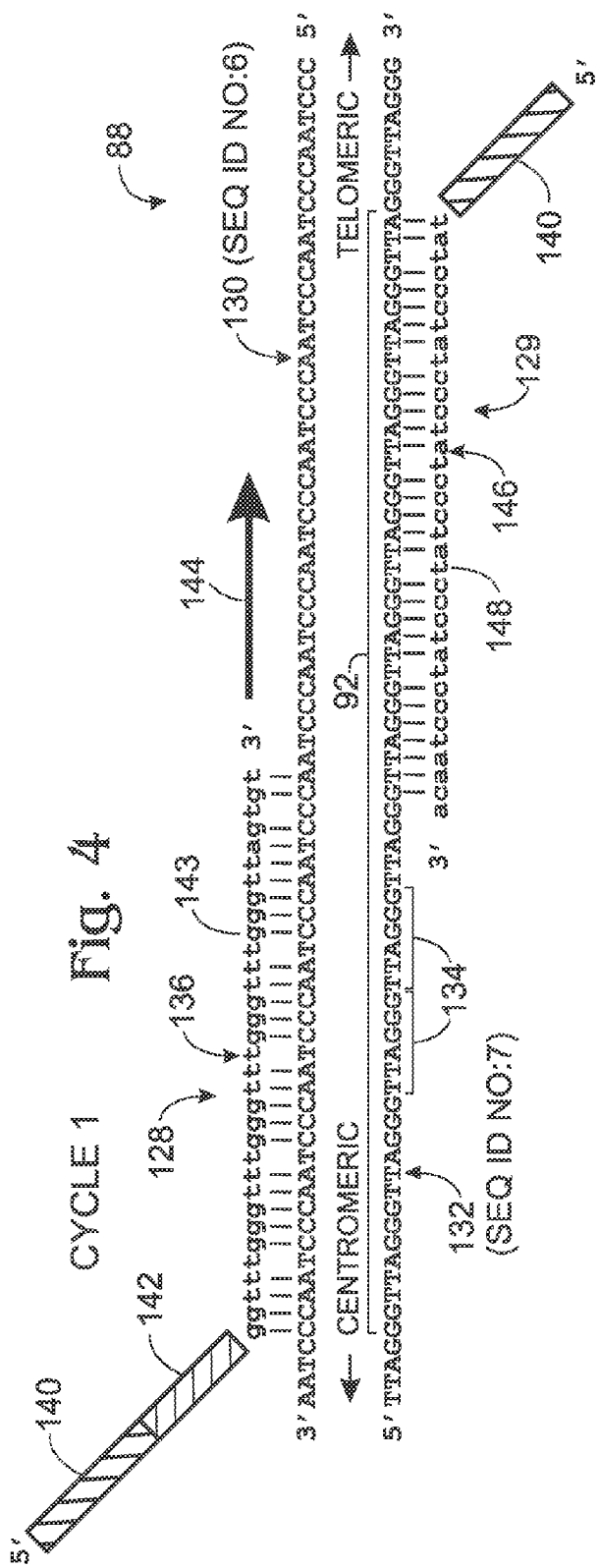
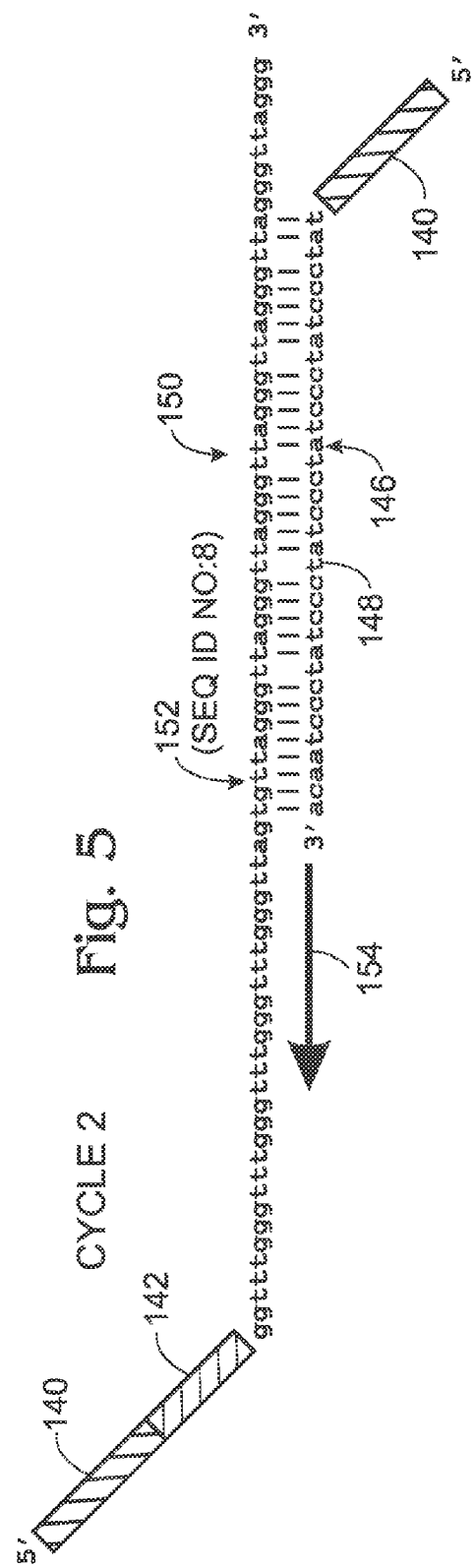

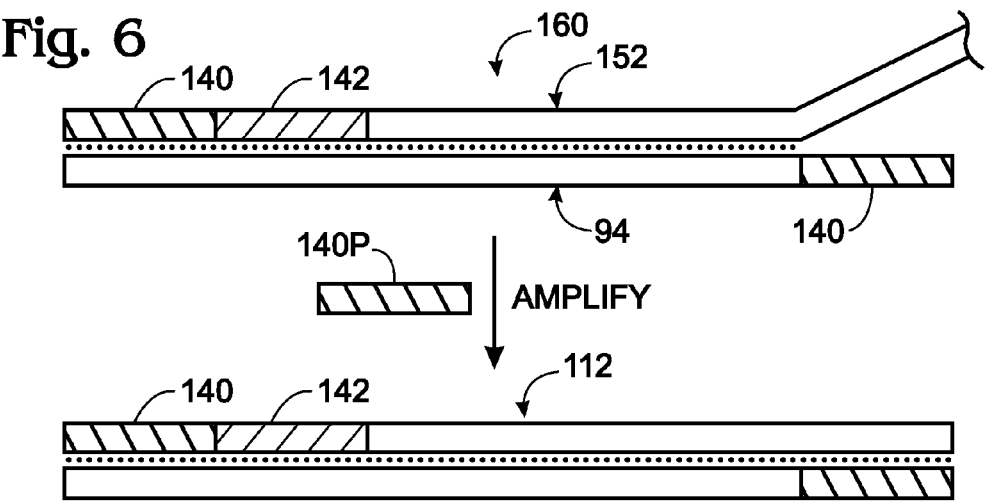
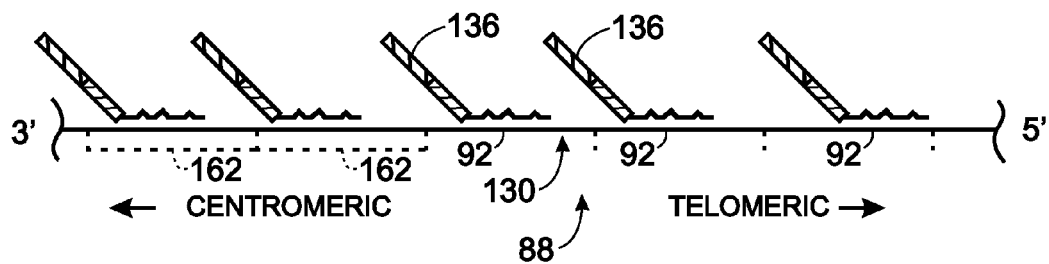
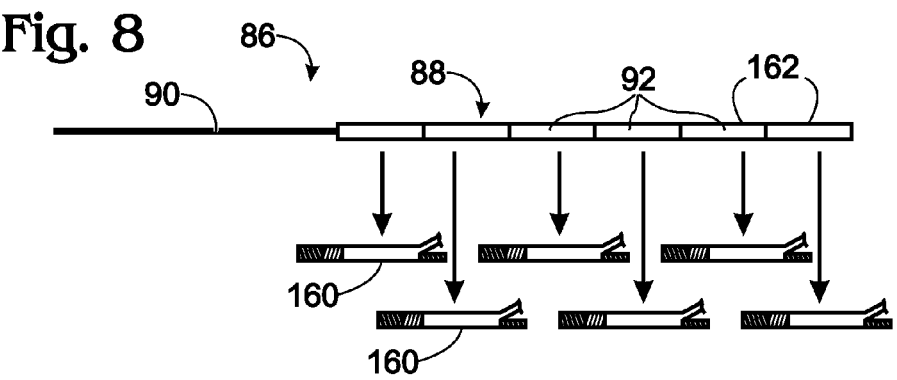

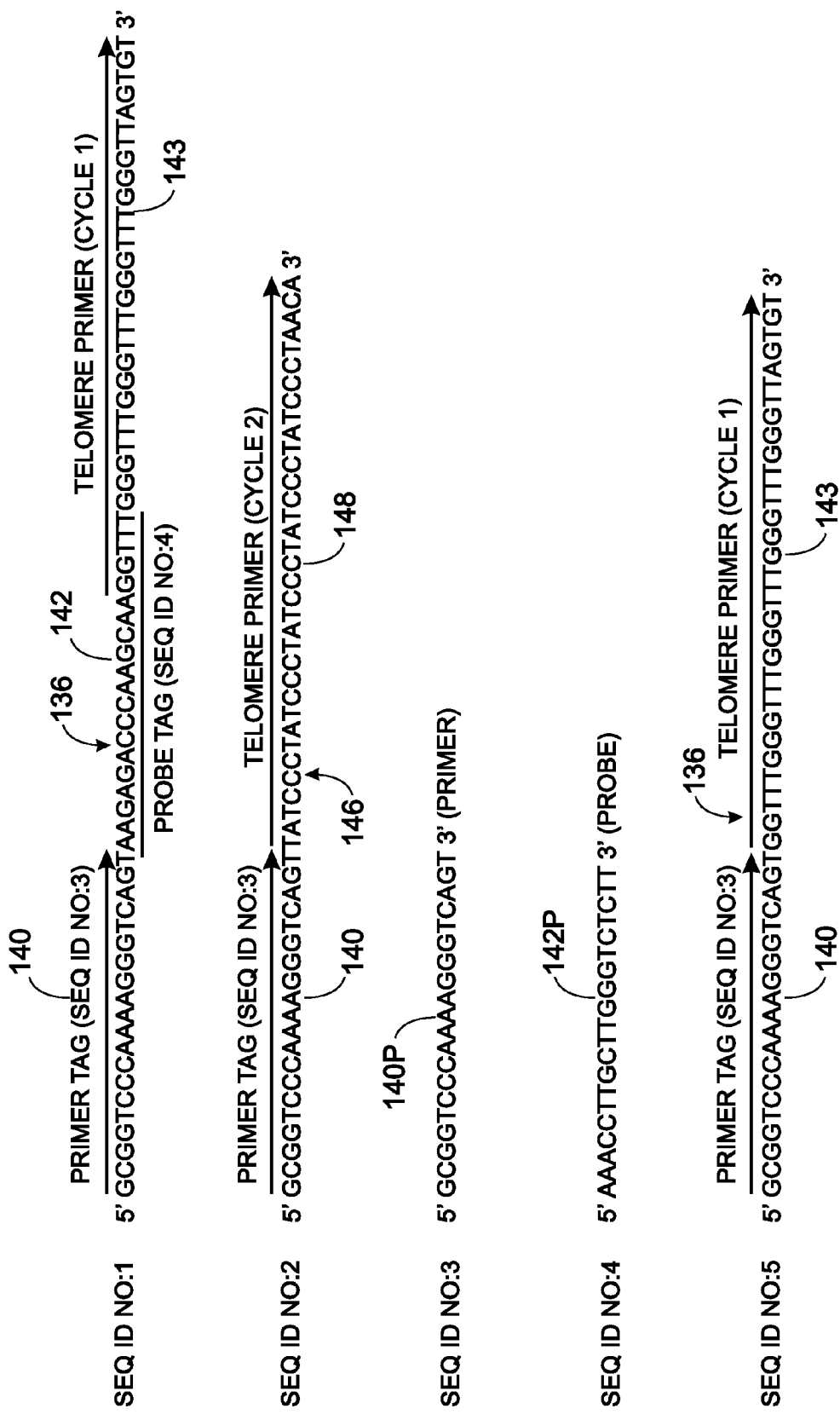

DIGITAL ASSAY FOR TELOMERE LENGTH

CROSS-REFERENCE TO PRIORITY APPLICATION

This application is based upon and claims the benefit under 35 U.S.C. §119(e) of U.S. Provisional Patent Application Ser. No. 61/759,768, filed Feb. 1, 2013, which is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; and Joseph R. Lakowicz, PRINCIPLES OF FLUORESCENCE SPECTROSCOPY ($2^{nd}$ Ed. 1999).

INTRODUCTION

Telomeres are the natural ends of a linear chromosome that serve to stabilize the chromosome. Each telomere is generally composed of a highly repetitive DNA sequence. For example, in vertebrates such as humans, a hexamer repeat (5' TTAGGG 3') is present hundreds or thousands of times in tandem at each chromosome end to generate telomeres that are kilobase pairs in length.

Telomeres also serve as binding sites for proteins that help maintain chromosomal integrity. The proteins prevent end-to-end joining, degradation, and recombination, among others, at the ends of chromosomes.

Telomere length can serve as an indicator of cell age. DNA polymerase cannot replicate the very end (e.g., the last 100 to 200 nucleotides or so) of a linear chromosome due to the lagging-strand problem. As a result, in most cell types, each telomere decreases in length every replication cycle, which is linked to the mitotic clock that limits the number of cell divisions permitted before a mortal cell undergoes senescence. Immortal cells, such as tumor cells and stem cells, can avoid this progressive telomere shortening through the action of an enzyme, telomerase, which adds copies of the basic telomere repeat to maintain or even increase telomere length as the immortal cells proliferate.

Telomere length can provide information about the age, health, and proliferative potential of cells. Accordingly, researchers have developed techniques to measure telomere length. In one approach, genomic DNA is treated with an enzyme that cuts near, but not in, each telomere, to produce approximately telomere-sized fragments that contain an intact telomere. The fragments are then sized by electrophoresis in the presence of size markers.

The measurement of telomere length for research and clinical purposes is becoming increasingly important. A new approach for determining telomere length is needed.

SUMMARY

The present disclosure provides a digital assay system, including methods and apparatus, for characterizing telomere length.

BRIEF DESCRIPTION OF THE DRAWINGS

FIG. 1 is a flowchart of steps that may be performed in an exemplary method of characterizing telomere length with a digital assay system, in accordance with aspects of the present disclosure.

FIG. 2 is a side-by-side schematic illustration of configurations that may be produced during performance of the method of FIG. 1 with a sample containing shorter telomeres and another sample containing longer telomeres, in accordance with aspects of the present disclosure.

FIG. 3 is a schematic illustration of an exemplary digital assay system for characterizing telomere length, in accordance with aspects of the present disclosure.

FIG. 4 is a somewhat schematic, fragmentary view of both strands of a telomere after the telomere has been denatured and the strands annealed to first and second primers (SEQ ID NO:1 and SEQ ID NO:2, respectively) during an exemplary first cycle of template synthesis performed in an exemplary digital assay for telomere length.

FIG. 5 is a fragmentary view of an intermediate generated by the first cycle of template synthesis of FIG. 4 and annealed with the second primer (SEQ ID NO:2) during an exemplary second cycle of template synthesis performed in an exemplary digital assay for telomere length.

FIG. 6 is a schematic view of amplification of a template to generate copies of an amplicon, with the template resulting from completion of the first and second cycles illustrated in FIGS. 4 and 5.

FIG. 7 is a fragmentary, schematic view of the leading strand of a telomere annealed to multiple copies of the first primer of FIG. 4 during the first cycle of template synthesis.

FIG. 8 is a schematic illustration of a template copy being generated from each of a plurality of telomere repeat regions.

FIG. 9 is list of exemplary primer and probe sequences for characterizing telomere length in a digital assay, in accordance with aspects of the present disclosure.

DETAILED DESCRIPTION

The present disclosure provides a digital assay system, including methods and apparatus, for characterizing telomere length.

An exemplary method of characterizing telomere length is provided. In the method, a template may be synthesized in the presence of genomic DNA. The template may represent a repetitive telomeric sequence present in the genomic DNA. Partitions may be formed, with only a subset of the partitions containing at least one copy of the template. At least a region of the template may be amplified in partitions. Amplification data may be collected from partitions. A measure of telomere length for the genomic DNA may be determined based on the data collected.

Another exemplary method of characterizing telomere length is provided. In the method, a template may be synthesized in the presence of a sample, with synthesis of the template dependent on a repetitive telomeric sequence in the sample. Partitions may be formed containing the template at partial occupancy. At least a region of the template may be amplified in the partitions to form an amplicon in only a subset of the partitions. Amplification data may be collected from partitions. A measure of telomere length for the sample may be determined based on the data collected.

The digital assays of the present disclosure for characterizing telomere length may have numerous advantages over other approaches, including any combination of higher throughput, better accuracy and/or sensitivity, and reduced use of consumables, among others.

Further aspects of the present disclosure are presented in the following sections: (I) overview of digital assays for characterizing telomere length and (II) examples.

I. Overview of Digital Assays for Characterizing Telomere Length

This section provides an overview of a digital assay system for characterizing telomere length; see FIGS. 1-3.

A measure of telomere length may be obtained from a digital assay. Digital assays generally rely on the ability to detect the presence or activity of individual copies of an analyte, such as a nucleic acid template (also termed a target), in a sample. In an exemplary digital assay, a sample is separated into a set of partitions, generally of equal volume, with each containing, on average, about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The negative fraction (or, equivalently, the positive fraction) then may be utilized to determine the concentration of the analyte in the partitions by Poisson statistics.

FIG. 1 shows a flowchart of steps that may be performed in an exemplary method 50 of characterizing telomere length with a digital assay system. The steps may be performed in any suitable order, in any suitable combination, and may be combined with or modified by any other suitable aspects of the present disclosure.

Sample Preparation.

A sample may be prepared for analysis of telomere length, indicated at 52. The sample, which may be described as a genomic DNA sample, may contain genomic DNA from any suitable source(s). Exemplary sources include one or more eukaryotic cells, such as a single cell, a group of cells (e.g., cultured cells, cells isolated from biological fluid, primary cells, a tissue sample, etc.), a biological fluid (e.g., blood, lymph, urine, semen, tears, mucus, saliva, etc.), a whole organism (e.g., a fungus (such as *Aspergillus* or *Saccharomyces cerevisiae*), a nematode (e.g., *C. elegans*), an insect (e.g., *Drosophila melanogaster*), a fish (e.g., zebrafish), a frog (e.g., *Xenopus laevis*), a mammal (e.g., a human or a mouse), or the like.

Preparation of the sample may include any suitable manipulation of the sample, such as collection, dilution, concentration, purification, lyophilization, freezing, extraction, cell lysis, precipitation of genomic DNA, combination with one or more assay reagents, shearing, sonication, performance of at least one preliminary reaction (e.g., fragmentation of genomic DNA by restriction enzyme digestion), or any combination thereof, among others. Preparation of the sample may include rendering the sample competent for subsequent performance of one or more reactions, such as one or more enzyme catalyzed reactions and/or binding reactions, e.g., synthesis of a template and/or amplification of the template.

Template Synthesis.

A template representing a repetitive telomeric sequence in the sample (and/or genomic DNA thereof) may be synthesized, indicated at 54. Synthesis of the template may be performed in a bulk phase (i.e., before sample partitioning) in the presence of suitable reagents, such as one or more primers to form the template, dNTPs (or NTPs), a polymerase (e.g., a heat-stable DNA polymerase), and the like. Copies of the template all may be perfect copies that are identical to one another or may include imperfect copies that result, for example, from sequence variation of the repetitive telomeric sequence in the sample.

Template synthesis may be performed in a reaction mixture. The reaction mixture (and/or genomic DNA of the sample) may be heated to a denaturation temperature, to denature the genomic DNA, cooled to an annealing temperature, to anneal one or more primers to the denatured genomic DNA, and heated to an extension temperature, to extend the one or more primers. In some cases, the annealing and extension temperatures may be the same. The reaction mixture (and/or genomic DNA of the sample) may be thermally cycled during template synthesis, to execute at least one or at least two cycles of denaturation, annealing, and extension. In exemplary embodiments, the denaturation temperature is about 90° C. to 99° C., the annealing temperature is about 35° C. to 60° C., and the extension temperature is about 60° C. to 80° C. In exemplary embodiments, the annealing temperature for at least one cycle or each cycle is less than the annealing temperature used for later amplification of the template. The synthesized template may or may not be purified from the reaction mixture before copies of the template are disposed in partitions.

Partition Formation.

Partitions containing copies of the template at partial occupancy may be formed, indicated at 56. A bulk phase (e.g., a template reaction mixture) prepared from the sample and containing the synthesized template may be divided or separated into partitions. Separation of the template may involve distributing any suitable portion, including up to the entire bulk phase, to the partitions. Each partition may be and/or include a fluid volume that is isolated from the fluid volumes of other partitions. The partitions may be isolated from one another by a fluid phase, such as a continuous phase of an emulsion, by a solid phase, such as at least one wall of a container, or a combination thereof, among others. In exemplary embodiments, the partitions may be droplets disposed in a continuous phase, such that the droplets and the continuous phase collectively form an emulsion.

In some embodiments, the bulk phase may contain particles (e.g., beads), which may, for example, be paramagnetic and/or composed of a polymer (e.g., polystyrene). The particles may be pre-attached to any suitable component(s), such as one or more types of primer, template(s), or the like, before bulk phase partitioning. The particles may be disposed in the partitions when the bulk phase is divided to form partitions, optionally with an average of about one particle (or less) per partition.

The partitions may be formed by any suitable procedure, in any suitable manner, and with any suitable properties. For example, the partitions may be formed with a fluid dispenser, such as a pipette, with a droplet generator, by agitation of the bulk phase (e.g., by shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 pL, among others.

The partitions, when first generated from the bulk phase, may be competent for performance of one or more reactions in the partitions. Alternatively, or in addition, one or more reagents may be added to the partitions after they are generated initially to render them competent for reaction. The reagents may be added by any suitable mechanism, such as a fluid dispenser, fusion of droplets, or the like, to form partitions that are ready for amplification.

The partitions may be formed with any suitable average number of template copies per partition. In some cases, the partitions may contain the template at partial occupancy. The term "partial occupancy" means that only a subset of the partitions formed contain at least one copy of the template. In other words, at least one or a plurality of the partitions contain no copies of the template, and at least one or a plurality of the partitions contain one or more copies of the template. In some cases, the partitions may contain an average per partition of less than about ten copies of the template when the step of amplifying is initiated. For example, the partitions may contain an average per partition of less than about five, three, two, or one copy of the template when the step of amplifying is initiated. The copies of the template may have a random distribution, such as a Poisson distribution, among the partitions.

In some embodiments, before the synthesized template is partitioned, a bulk phase containing the template may be combined with reagents for amplification and for reporting whether or not amplification occurred. Reagents for amplification may include any combination of one or more primers for amplicon amplification from the template, dNTPs or NTPs, at least one enzyme (e.g., a polymerase, a ligase, or a combination thereof, each of which may or may not be heat-stable), and/or the like. Accordingly, a bulk phase containing the template may be rendered capable of amplification of the template, if present, in the bulk phase (or a partition thereof). Reagents for reporting may include a reporter for amplification of the amplicon. Preparation of the bulk phase for reporting may render the bulk phase capable of reporting, or being analyzed for, whether or not amplification has occurred, for the template, and optionally the extent of any such amplification. The reporter may interact at least generally nonspecifically or specifically with the template (and/or or an amplicon generated by amplification thereof). In some cases, the reporter may be a generic reporter (e.g., an intercalating dye) having a general affinity for nucleic acid (single and/or double-stranded) without substantial sequence-specific binding. In some cases, the reporter may be a probe that includes a nucleic acid (e.g., an oligonucleotide) attached to a label, such as labeled with a photoluminophore (e.g., a fluorophore or phosphor).

Amplification.

The template may be amplified in the partitions to form an amplicon corresponding to the template, indicated at 58. Template amplification interchangeably may be termed amplicon amplification that generates an amplified template or amplicon. Template amplification may amplify any suitable region of the template or may amplify the entire template. Amplification of the template may occur selectively (and/or substantially) in only a subset of the partitions, such as less than about nine-tenths, three-fourths, one-half, one-fourth, or one-tenth of the partitions, among others. In some examples, the amplification reaction may be a polymerase chain reaction and/or ligase chain reaction.

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Data Collection.

Data for template amplification may be collected from partitions, indicated at 60. The data may be collected from individual partitions and indicate whether a given partition is amplification-positive or amplification-negative. The data may be collected by detecting light and creating one or more signals representative of light detected from the partitions. The signal may represent an aspect of light, such as the intensity, polarization, and/or lifetime of light, and/or a property thereof, emitted from the partitions in response to illumination with excitation light. The signal may be created based on detected light emitted from a reporter in the partitions. Exemplary reporters include a dye that binds double-stranded DNA (e.g., an intercalating dye), a photoluminophore-labeled probe, or the like.

Partitions may be analyzed and signals created at any suitable time(s). Exemplary times include at the end of an assay (endpoint assay), when reactions have run to completion and the data no longer are changing, or at some earlier time, as long as the data are sufficiently and reliably separated. For example, data may be collected from partitions (e.g., light may be detected from the partitions) after target amplification has reached an endpoint. All of the data may be collected from the partitions at about the same temperature.

Telomere Length Determination.

A measure of telomere length for the genomic DNA may be determined, indicated at 62. The measure may be an absolute or relative measure of telomere length. Also, the measure for the genomic DNA may represent an average telomere length for a source of the genomic DNA, because telomeres of the genomic DNA itself may be fragmented during preparation. The measure may, for example, be expressed as an average length value in nucleotides or nucleotide base pairs per telomere for the genomic DNA. Alternatively, or in addition, the measure may be expressed as a ratio involving a number of template copies synthesized and an amount of genomic DNA present during template synthesis. The amount of genomic DNA may be expressed according to mass (e.g., in picograms), genome-equivalents, or the like.

A level of the template in partitions may be determined based on the data collected. More particularly, a concentration of the template in partitions may be determined based on the presence or absence of the corresponding amplicon in each partition. A fraction of the partitions that are negative (or, equivalently, positive) for the amplicon may be calculated. The fraction may be calculated as the number of negative (or, equivalently, positive) partitions for the amplicon divided by a total number of partitions.

A concentration of the template may be calculated with Poisson statistics. The concentration may be expressed with respect to the partitions and/or with respect to a sample providing the genomic DNA. The concentration of the template in the partitions may be calculated from the fraction of positive partitions by assuming that template copies have a Poisson distribution among the partitions. With this assumption, the fraction f(k) of partitions having k copies of the template is given by the following equation:

$$f(k) = \frac{c^k}{k!}e^{-c} \qquad (1)$$

Here, C is the concentration of the template in the partitions, expressed as the average number of template copies per partition. Simplified Poisson equations may be derived from the more general equation above and may be used to determine template concentration from the fraction of positive partitions. An exemplary Poisson equation that may be used is as follows:

$$C = -\ln\left(1 - \frac{N_+}{N_{tot}}\right) \qquad (2)$$

where $N_+$ is a number of positive partitions and $N_{tot}$ is a total number of partitions, such that $N_+/N_{tot}$ is equal to $f_p$, which is the fraction of partitions positive for the template (i.e., $f_p = f(1) + f(2) + f(3) + \ldots$), and which is a measured estimate of the probability of a partition having at least one copy of the template. Another exemplary Poisson equation that may be used is as follows:

$$C = -\ln\left(\frac{N_0}{N_{tot}}\right) \qquad (3)$$

where $N_0$ is a number of negative partitions and $N_{tot}$ is a total number of partitions, such that $N_0/N_{tot}$ is equal to $f_n$, which is the fraction of negative droplets (or $1-f_p$), which is a measured estimate of the probability of a partition having no copies of the template, and C is the concentration as described above.

In some embodiments, an estimate of the concentration of the template may be obtained directly from the positive fraction, without use of Poisson statistics. In particular, the positive fraction and the concentration (copies per partition) converge as the concentration decreases. For example, with a positive fraction of 0.1, the concentration is determined with the above equation to be about 0.105, a difference of only 5%; with a positive fraction of 0.01, the concentration is determined to be about 0.01005, a ten-fold smaller difference of only 0.5%. However, use of a Poisson equation can provide a more accurate estimate of concentration, particularly with a relatively higher positive fraction, because the equation accounts for the occurrence of multiple template copies per partition.

The concentration of template (copies per partition) determined then may be utilized to calculate a measure of telomere length. For example, a number of copies of the template synthesized relative to an amount of genomic DNA used for synthesis may be calculated. As an example, intended for illustration only, if 1 pg of human genomic DNA from a first human sample is represented by 10,000 partitions, and the partitions have an average concentration of 0.4 copies of the template, 4,000 template copies were produced per picogram of the genomic DNA, or about 13,000 template copies per genome-equivalent (a haploid genome-equivalent of human DNA is about 3.3 pg). A second human sample that produced only 2,000 template copies per picogram of genomic DNA, under the same assay conditions, has telomeres that are only one-half as long as those of the first sample, while a third human sample with 8,000 template copies per picogram of genomic DNA has telomeres that are twice as long, on average, as those of the first sample. Accordingly, the number of template copies generated per unit amount of genomic DNA can be a measure of telomere length.

The amount of genomic DNA present in the sample and/or in partitions may be determined using any suitable test. The test may be performed with or without amplification. An exemplary approach for measuring genomic DNA content in the sample without amplification uses a dye that fluoresces in the presence of DNA. If performed with amplification, the amplification may be conducted in partitions or in bulk phase (e.g., by quantitative PCR). If performed in partitions, the partitions may be from the same set of partitions used for assaying the template, or may be partitions formed separately. In some cases, the amount of genomic DNA may be measured in partitions by digital assay of a target with a known copy number in the genome. For example, a target representing a single-copy gene would be expected to produce about one positive partition per genome-equivalent of genomic DNA analyzed.

The measure of telomere length may be determined based on a value obtained from a standard having a known telomere length. The value may be determined in a test performed by the user or may be obtained from a third party. If performed by the user, telomere length may be determined by any suitable test, such as sizing whole-telomere fragments through electrophoresis and comparison with size markers. Genomic DNA from the standard also may be tested, by the user or a third party, to determine a measure of telomere length in a digital assay system. As an example, intended only for illustration, a standard (e.g., an established human cell line) may have telomeres with a known average length of 12 kilobase pairs (kb). One genome-equivalent (3.3 pg, if human) of genomic DNA from the standard may be found to generate 4600 template copies, as measured in the digital assay system. Therefore, the standard supplies a value for converting between (a) a number of template copies produced per genome-equivalent (or "genome") and (b) an average telomere length in kilobase pairs:

4600 template copies/(genome)(12 kb)=380 copies/
(genome)(kb) (4)

The value from the standard then can be utilized to calculate an average telomere length. For example, if a sample when assayed is found to produce 8200 template copies per genome-equivalent, then the average telomere length of the sample may be calculated as (8200/380) kb, or 22 kb. In some cases, a conversion value from a standard for one species may be applied to determining a telomere length for a sample from another, different species, by adjusting for inter-species differences in chromosome number per genome and genome size.

The standard also or alternatively may provide a value that expresses a relationship between the template copies and an average length of a telomere region from which each copy was synthesized. The numbers from the preceding paragraph are used again here for illustration. A (haploid) human genome has 23 chromosomes, which carry 46 telomeres (one at each chromosome end). Each genome-equivalent of the standard may, for example, produce 4600 template copies from 46 telomeres, or about 100 template copies per individual telomere. Since the standard in the present illustration has an average telomere length of 12 kb, each template copy represents 0.12 kb of telomere sequence.

Further aspects of sample preparation, droplet generation, data collection, and template level determination, among others, that may be suitable for the system of the present disclosure are described in the references listed above under Cross-References, which are incorporated herein by reference.

FIG. 2 shows a pair of side-by-side schematic flow diagrams of exemplary configurations 64-78 that may be produced during performance of method 50 with a pair of samples 80, 82 containing respective genomic DNAs 84, 86 having different average lengths of telomeres 88. More particularly, genomic DNA 84 provides telomeres 88 having a relatively shorter average length, and genomic DNA 86 has telomeres 88 with a relatively longer average length. The length of the telomeres is defined for intact, non-fragmented telomeres, as found in full-length chromosomes, whether or not telomere fragmentation has occurred during preparation of the genomic DNA. Each sample may, for example, be an aqueous sample.

Configurations 64, 66 of FIG. 2 schematically depict each of genomic DNAs 84, 86 as an intact single chromosome having opposing end regions formed by telomeres 88 and an intervening region 90 extending between the telomeres. However, the genomic DNA is more generally composed of chromosome fragments of any suitable size, which may or may not include fragments produced by cutting or breaking the genomic DNA within telomeres. Also, the genomic DNA in the sample may represent any suitable number of genome-equivalents and thus any number of chromosomes. A genome-equivalent of genomic DNA from a source (e.g., a single cell, a group of cells, a tissue sample, a whole organism, or the like) is the amount of genomic DNA present in a single copy of the genome of the source. Accordingly, for a diploid source, such as a human subject, with two copies of each chromosome per cell (and thus two genomes per cell), two genome-equivalents contain an average of about two copies of each single-copy gene of the subject's genome. Furthermore, FIG. 2 does not distinguish double-stranded from single-stranded DNA.

Each telomere 88 has a repetitive structure indicated schematically. The telomere may have a tandem arrangement of telomere repeat sequences 92 of any suitable length. Telomeres are generally composed of basic repeats, such as hexamer repeats, which form higher-order repeats containing multiple copies of the basic repeat. Accordingly, telomere repeat sequence 92 may have any suitable number of the basic repeats and may have any suitable length, such as at least about 25 to 1000 nucleotides, among others. In exemplary embodiments, telomere repeat sequence 92 is about 50 nucleotides or less and thus would be repeated about 100 times or more in a telomere of 5 kilobase pairs.

Configurations 68, 70 show copies of a template 94 synthesized (interchangeably termed "pre-amplified") with genomic DNA 84, 86 of each sample 80, 82. Each template 94 represents a copy of telomere repeat sequence 92 present in telomere 88. The number of copies of template 94 synthesized is directly related, such as proportional, to the number of copies of telomere repeat sequence 92 present in the genomic DNA. For example, in the highly simplified embodiment illustrated here, six copies of template 94 are synthesized from shorter telomeres 88 of sample 80 (configuration 68), and twice as many copies (12 copies) of template 94 from longer telomeres 88 of sample 82 (configuration 70). Therefore, the number of copies of template 94 can reflect the mass of telomeres present in the sample (i.e., the telomeric content of the sample). Alternatively, or in addition, the number of copies of template 94 synthesized relative to the number of genome-equivalents used to synthesize that number of copies, reflects the telomere length of the sample. For example, in the highly simplified embodiment illustrated here, two telomeres provided by one genome-equivalent (sample 80) generate three copies of template 94 per telomere (configuration 68), and two telomeres of sample 82 generate six copies of template 94 per telomere (configuration 70), because the telomeres of sample 82 are twice as long as those of sample 80.

Configurations 72, 74 show respective emulsions 100, 102 generated from samples 80, 82 after synthesis of template 94. Each emulsion contains a plurality of droplets 104 disposed in a continuous phase 106. The droplets are formed at a partial occupancy of template 94, such that only a subset of the droplets contains one or more copies of template 94. For example, in configuration 72, six of the droplets contain one copy of the template and the other droplets contain no template copies. In configuration 74, where there are twice as many template copies, two of the droplets, such as the droplet indicated by an arrow at 108, contain more than one copy of template 94. In any event, copies of template 94 may be assumed to have a Poisson distribution among the droplets (or other partitions) formed.

Configurations 76, 78 show emulsions 100, 102 after amplification of template 94. Droplets 104 containing at least one copy of template 94 now contain amplified template, namely, copies of an amplicon 112. Each amplification-positive droplet then may be identified by detecting a characteristic of each droplet, such as detecting a characteristic of light 114 from the droplet. The characteristic may, for example, be intensity, polarization, absorbance, scattering, or the like, and may reflect a current or integrated value or a lifetime, among others. The light may be emitted from a photoluminescent reporter present in the droplet. The reporter may, for example, be an intercalating dye, a dye-labeled probe, or the like. A dye-labeled probe may include an oligonucleotide associated with a dye. A dye may be described interchangeably as a luminophore.

Multiple-occupancy droplets, such as droplet 108, that initially received more than one copy of template 94, may be substantially indistinguishable from droplets that received only one copy of template 94. However, Poisson statistics can be used to calculate the average concentration of template copies in the droplets based on the fraction of droplets that are determined to be negative for template amplification.

FIG. 3 shows an exemplary system 120 for performing any suitable combination of steps of the digital assay of FIG. 2. System 120 may include a partitioning assembly, such as a droplet generator 122 ("DG"), a thermal incubation assembly, such as a thermocycler 124 ("TC"), a detection assembly (a detector) 126 ("DET"), and a data processing assembly (a processor) 128 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets) or signals/data, between the assemblies. Any suitable combination of the assemblies may be operatively connected to one another, and/or one or more of the assemblies may be unconnected to the other assemblies, such that, for example, material/data is transferred manually.

Apparatus 120 may operate as follows. A template may be synthesized in a bulk phase in thermocycler 124. Droplet generator 122 may form droplets of the bulk phase disposed in a continuous phase, with the droplets containing the template at partial occupancy. The droplets may be cycled thermally with thermocycler 124, to promote amplification of an amplicon corresponding to the template in the droplets. Data may be collected from the droplets with detector 126. The data may be processed by processor 128 to determine numbers of droplets, a template level(s), an amount of genomic DNA, and/or a measure of telomere length, among others.

II. Examples

The following examples describe selected aspects of digital assays to characterize telomere length. These examples are intended for illustration only and should not limit the entire scope of the present disclosure.

Example 1

Exemplary Primers and Probes

This example describes exemplary primers and probes, and resulting templates and synthesis configurations for performing a digital assay for telomere length; see FIGS. 4-9.

FIGS. 4 and 5 respectively show exemplary annealed configurations generated during a first cycle and a second cycle of template synthesis. Each cycle may be described as a thermal cycle during which a sample and/or reaction mixture is heated to a denaturation temperature (to melt double-strands), cooled to an annealing temperature (to anneal a primer(s)), and heated to an extension temperature. The temperatures may, for example, be about 90° C. to 100° C. for the denaturation temperature, about 35° C. to 75° C. for the annealing temperature, and about 60° C. to 80° C. for the extension temperature, among others. In some embodiments, the annealing temperature and the extension temperature may be the same. In exemplary embodiments, the annealing temperature is about 45° C. to permit formation of a mismatched duplex.

FIG. 4 shows a pair of annealed configurations 128, 129 of strands of a portion of telomere 88 during a first cycle of template synthesis (also see FIG. 1). Telomere 88 is composed of a leading strand 130 and a lagging strand 132, named according to their respective roles during telomere replication. The leading strand of the telomere has a 5'-region that is farther from the chromosome centromere than the 3'-region of the strand. The lagging strand of the telomere has a 5'-region that is closer to the centromere than the 3'-region of the strand. Here, the telomere has been denatured (e.g., by heating) to separate the leading and lagging strands from one another to form single strands.

FIG. 4 shows telomere 88 as a vertebrate telomere, such as a human telomere, having a basic repeat 134 of six nucleotides, namely, a hexamer repeat with the sequence 5' TTAGGG 3'. The basic repeats are fused to one another as direct repeats to form higher-order repeats having multiple copies of the hexamer repeat. For example, telomere repeat sequence 92 is a higher-order repeat composed of ten copies of basic repeat 134 (plus a partial copy at each end).

Annealed configuration 128 is created by a first cycle primer 136 binding to leading strand 130. Primer 136 may be composed of a primer tag 140, a probe tag 142, and a repeat binding region 143. Tags 140, 142 and binding region 143 may be attached to one another covalently. Primer tag 140 introduces a primer sequence to allow template amplification with a suitable primer after the template is synthesized and distributed to partitions. Probe tag 142 introduces a probe binding site to allow template amplification to be detectable with a suitable probe. The introduction of a probe binding site is optional.

Binding region 143 binds to leading strand 130 to form an imperfect duplex that is mismatched at a plurality of nucleotide positions (five are illustrated here). However, the 3' end of binding region 143 is based-paired with leading strand 130, which permits the leading strand to be extended, indicated by an arrow at 144, by a DNA polymerase during the first cycle of template synthesis.

Annealed configuration 129 is created by a second cycle primer 146 binding to lagging strand 132. The second cycle primer may be composed of primer tag 140 and a repeat binding region 148. The final nucleotide at the 3'-end of repeat binding region 148 is not based-paired with lagging strand 132. Accordingly, when primer 136 is extended by DNA synthesis during the first cycle of template synthesis, second cycle primer 146 is not extended. In other embodiments, the first cycle primer may bind to the lagging strand and may use the lagging strand to template primer extension.

FIG. 5 shows a fragmentary view of an annealed configuration 150 produced during the second cycle of template synthesis. The annealed configuration results from second cycle primer 146 binding to an extension product 152 synthesized by the first cycle of template synthesis (e.g., see arrow 144 of FIG. 4). The extension product may be substantially longer than shown at its 3' end and may be variable in length. Second cycle primer 146 forms a mismatched duplex with extension product 152. However, the 3' end of primer 146 is based-paired with extension product 150, which allows polymerase to extend second cycle primer 146, indicated by an arrow at 154, to the 5' end of the extension product, with the extension product templating synthesis.

FIG. 6 schematically illustrates amplification of template 94 to generate copies of amplicon 112. Template 94 is provided by a template-containing duplex 160 that results from extending primers 136, 146 during the first and second cycles of template synthesis (see FIGS. 4 and 5). Base pairs formed within duplex 160 are depicted schematically as dots, which do not reflect the number of base pairs formed. Duplex 160, which is partially single-stranded at only one end, is composed of extension product 152 created by the first cycle of template synthesis, and template 94 created by the second cycle of template synthesis. Template 94 has primer tag 140 at the 5' end and a sequence complementary to tag 140 at the 3' end. Accordingly, a single primer 140P can be utilized to amplify template 94 to generate copies of amplicon 112. An annealing temperature used for amplification of amplicon 112 may be higher than an annealing temperature used for synthesis of the template. For example, the annealing temperature for amplification of the amplicon may be about 60° C. to 75° C., among others.

FIG. 7 shows an exemplary configuration in which multiple copies of first cycle primer 136 may bind to leading strand 130 of telomere 88, to permit synthesis of copies of an extension product suitable for the second cycle. Copies of primer 136 may bind copies of telomere repeat sequence 92 with a variable separation between the primer copies. However, on average, the copies of first primer 136 may bind productively (to produce a functional extension product 152 for the second cycle) about once per each interval 162. The interval may, for example, be about 25 to 1000 nucleotides, among others. The size of the interval may be adjusted, such as by changing the length of the primer's binding region, by changing the number of base-pair mismatches, by changing the ratio of primer to leading strand, or the like. (If the primers bind too closely to each other, the polymerase may be unable to extend to form an extension product 152 of sufficient length for primer 146 to bind during the second cycle (see FIG. 5).)

FIG. 8 shows an exemplary relationship between each interval 162 (also see FIG. 7) and production of a template-containing duplex 160. More particularly, an average of one copy of template-containing duplex 160 may be formed from each interval 162.

FIG. 9 presents a list of exemplary primer and probe sequences for characterizing telomere length in a digital assay. SEQ ID NO:1 is an exemplary first cycle primer 136. SEQ ID NO:2 is an exemplary second cycle primer 146. SEQ ID NO:3 is an exemplary primer 140P that is identical in sequence to primer tag 140 of SEQ ID NO:1 and SEQ ID NO:2. SEQ ID NO:4 is an exemplary probe 142P that is identical in sequence to probe tag 142 of SEQ ID NO:1. SEQ ID NO:5 is an exemplary first cycle primer 136 containing primer tag 140 but not probe tag 142.

Example 2

Selected Embodiments a

This example describes selected embodiments of a method of characterizing telomere length, presented as a series of numbered paragraphs.

1. A method of characterizing telomere length, the method comprising: (A) synthesizing a template in the presence of genomic DNA, the template representing a repetitive telomeric sequence present in the genomic DNA; (B) forming partitions containing the template at partial occupancy; (C) amplifying in the partitions an amplicon corresponding to the template; (D) collecting data for amplification of the amplicon in the partitions; and (E) determining a measure of telomere length for the genomic DNA based on the data collected.

2. The method of paragraph 1, wherein the step of determining a measure of telomere length includes a step of determining a concentration of the template in the partitions based on the collected data.

3. The method of paragraph 2, wherein the step of determining a measure of telomere length includes a step of determining a number of copies of the template in partitions based on the concentration and a step of determining an amount of the genomic DNA present in such partitions.

4. The method of paragraph 3, wherein the genomic DNA is provided by a sample, and wherein the amount of the genomic DNA is determined with data for amplification of a reference target in partitions containing the sample.

5. The method of paragraph 4, wherein the data for amplification of the template is collected from a first set of partitions, and wherein the data for amplification of a reference target is collected from a second set of partitions formed separately from the first set of partitions.

6. The method of paragraph 4, wherein the reference target is present once per genome in a source of the genomic DNA.

7. The method of paragraph 3, wherein the step of determining a measure of telomere length includes a step of determining a ratio based on the number of copies of the template and the amount of the genomic DNA, and wherein the ratio is the measure of telomere length.

8. The method of paragraph 3, wherein the measure of telomere length is a length value representing an average number of nucleotides or nucleotide base pairs present in telomeres of a source of the genomic DNA, and wherein the length value is calculated based on the number of copies of the template and the amount of genomic DNA.

9. The method of paragraph 8, wherein the length value is calculated based on a value from a standard.

10. The method of paragraph 9, wherein the standard has a known average telomere length.

11. The method of paragraph 1, wherein the measure of telomere length represents a relative length measurement.

12. The method of paragraph 1, wherein the measure of telomere length represents an absolute length measurement.

13. The method of paragraph 1, wherein the genomic DNA is a first genomic DNA from a first source, further comprising a step of performing the steps of synthesizing, forming, amplifying, and collecting for a second genomic DNA from a second source, and wherein the step of determining a measure of telomere length for the first genomic DNA is based on data collected with the second genomic DNA from the second source.

14. The method of paragraph 1, wherein the genomic DNA includes telomeres composed of a basic repeat, and wherein the telomere repeat sequence includes two or more tandem copies of the basic repeat.

15. The method of paragraph 14, wherein the basic repeat is a hexamer repeat having the sequence 5' TTAGGG 3', and wherein the telomere repeat sequence includes three or more tandem copies of the hexamer repeat.

16. The method of paragraph 1, wherein the genomic DNA is provided by a sample, further comprising a step of determining an amount of genomic DNA present in the sample and/or partitions thereof.

17. The method of paragraph 16, wherein the amount is determined with data collected from sample-containing partitions.

18. The method of paragraph 16, wherein the amount is determined with data collected from partitions formed separately from the partitions containing the template at partial occupancy.

19. The method of paragraph 16, wherein the amount of genomic DNA present in the sample is determined in an assay that does not include amplification of nucleic acid.

20. The method of paragraph 1, wherein the step of determining uses a value obtained from at least one standard having a known telomere length.

21. The method of paragraph 20, wherein the value is supplied by a third party.

22. The method of paragraph 20, wherein the value is a factor that allows conversion of (a) a number of copies of the template synthesized per amount of the genomic DNA to (b) an average length of telomeres present in a source of the genomic DNA.

23. The method of paragraph 20, wherein the value represents a number of copies of the template that are amplified per unit length of telomere sequence present in the genomic DNA.

24. The method of paragraph 1, wherein the step of synthesizing is performed such that a number of copies of the template synthesized per genome-equivalent of the genomic DNA is related to a copy number of the telomere repeat sequence in the genome-equivalent.

25. The method of paragraph 24, wherein about one copy of the template is synthesized per 25 to 1000 base pairs of telomere DNA present in the genomic DNA.

26. The method of paragraph 1, wherein the data collected allows determination of a value for a fraction of the partitions that are negative partitions containing no copies of the template.

27. The method of paragraph 1, wherein the genomic DNA is provided by a sample, wherein the step of synthesizing includes a step of thermally cycling the sample for at least two cycles, and wherein the sample is heated to a denaturation temperature and cooled to an annealing temperature in each cycle.

28. The method of paragraph 27, wherein the step of amplifying includes a step of thermally cycling the partitions with an annealing temperature that is higher than the annealing temperature used in thermally cycling the sample for at least two cycles.

29. The method of paragraph 1, wherein the step of amplifying is performed in the presence of an intercalating dye.

30. The method of paragraph 1, wherein the step of amplifying is performed in the presence of a photoluminescent probe containing an oligonucleotide that binds specifically to a strand of the amplicon.

31. The method of paragraph 30, wherein the oligonucleotide binds to, or has sequence identity to, a region of the amplicon introduced by a tag portion of a primer used for the step of synthesizing, and wherein the tag portion is not required for the step of synthesizing.

32. The method of paragraph 1, wherein the template is a first target, further comprising a step of determining a level of a second target in the genomic DNA based on amplification data collected from the partitions, and wherein the level of the second target indicates a number of genome-equivalents represented by the genomic DNA.

33. The method of paragraph 1, wherein the template includes a strand of nucleic acid having a fixed length.

34. The method of paragraph 1, wherein the template is synthesized with a first primer that binds to and is extended past the telomere repeat sequence, to produce an extension product, and a second primer that binds to the extension product and is extended to an end of the extension product.

35. The method of paragraph 1, wherein the amplicon is composed of a pair of complementary strands, and wherein the step of amplifying is performed with a single primer that binds to both strands of the amplicon.

36. The method of paragraph 1, wherein the genomic DNA is obtained from a source that is any combination of a single cell or a plurality of cells, a tissue sample, a biological fluid, and one or more organisms.

37. The method of paragraph 1, wherein the partitions are droplets.

Example 3

Selected Embodiments B

This example describes selected embodiments of a method of characterizing telomere length, presented as a series of numbered paragraphs.

1. A method of characterizing telomere length, the method comprising: (A) synthesizing a template in the presence of genomic DNA, the template representing a repetitive telomeric sequence present in the genomic DNA; (B) forming partitions, with only a subset of the partitions containing at least one copy of the template; (C) amplifying at least a region of the template in partitions; (D) collecting amplification data from partitions; and (E) determining a measure of telomere length for the genomic DNA based on the amplification data.

2. A method of characterizing telomere length, the method comprising: (A) synthesizing a template in the presence of a sample, with synthesis of the template dependent on a repetitive telomeric sequence from the sample; (B) forming partitions containing the template at partial occupancy; (C) amplifying at least a region of the template in the partitions to form an amplicon in only a subset of the partitions; (D) collecting amplification data from partitions; and (E) determining a measure of telomere length for the sample based on the amplification data.

3. The method of paragraph 1 or 2, wherein each copy of the template represents an instance of a region of a telomere.

4. The method of any of paragraphs 1 to 3, wherein the genomic DNA or the sample is a genomic DNA sample, and wherein each copy of the template represents a single instance of the repetitive telomeric sequence in the genomic DNA sample.

5. The method of any of paragraphs 1 to 4, wherein the genomic DNA or the sample is obtained from a source that is any combination of a single cell or a plurality of cells, a tissue sample, a biological fluid, and one or more organisms.

6. The method of any of paragraphs 1 to 5, wherein the genomic DNA or the sample is provided at least in part by a source having a genome with a plurality of telomeres, with each telomere including multiple instances of the repetitive telomeric sequence.

7. The method of any of paragraphs 1 to 6, wherein the genomic DNA or the sample includes telomeres and/or telomere fragments composed of a basic repeat, and wherein the repetitive telomeric sequence includes two or more tandem copies of the basic repeat.

8. The method of paragraph 7, wherein the basic repeat is a hexamer repeat having the sequence 5' TTAGGG 3', and wherein the repetitive telomeric sequence includes three or more tandem copies of the hexamer repeat.

9. The method of any of paragraphs 1 to 8, wherein the step of synthesizing a template is performed such that a number of copies of the template synthesized per genome-equivalent of the genomic DNA is related to a copy number of the repetitive telomeric sequence in the genome-equivalent.

10. The method of paragraph 9, wherein about one copy of the template is synthesized per 25 to 1000 base pairs of telomeric DNA present in the genomic DNA.

11. The method of any of paragraphs 1 to 10, wherein the template includes a strand of nucleic acid having a fixed length.

12. The method of any of paragraphs 1 to 11, wherein the template is synthesized with a first primer that binds to and is extended past an instance of the repetitive telomeric sequence, to produce an extension product, and with a second primer that binds to the extension product and is extended to an end of the extension product.

13. The method of any of paragraphs 1 to 12, wherein the partitions are droplets.

14. The method of any of paragraphs 1 to 13, wherein the step of synthesizing a template is performed in a reaction mixture, wherein the step of synthesizing a template includes a step of thermally cycling the reaction mixture for at least two cycles, and wherein the reaction mixture is heated to a denaturation temperature and cooled to an annealing temperature in each cycle.

15. The method of paragraph 14, wherein the step of amplifying includes a step of thermally cycling partitions using an annealing temperature that is higher than the annealing temperature used in thermally cycling the reaction mixture for at least two cycles.

16. The method of any of paragraphs 1 to 15, wherein the step of amplifying is performed in the presence of an intercalating dye.

17. The method of any of paragraphs 1 to 16, wherein the step of amplifying is performed in the presence of a photoluminescent probe containing an oligonucleotide that binds specifically to at least one strand of an amplicon formed by template amplification.

18. The method of paragraph 17, wherein the oligonucleotide binds to, or has sequence identity to, a region of the amplicon introduced by a tag portion of a primer used for the step of synthesizing a template, and wherein the tag portion is not required for the step of synthesizing a template.

19. The method of any of paragraphs 1 to 18, wherein the amplification data allows determination of a value for a fraction of the partitions that are negative partitions containing no copies of the template.

20. The method of any of paragraphs 1 to 19, wherein the template provides a first target, further comprising a step of determining a level of a second target in the genomic DNA based on amplification data collected from partitions, and wherein the level of the second target indicates a number of genome-equivalents represented by the genomic DNA.

21. The method of any of paragraphs 1 to 20, wherein the step of amplifying forms an amplicon that includes a pair of complementary strands, and wherein the step of amplifying is performed with a single primer that binds specifically to each strand of the pair of complementary strands.

22. The method of any of paragraphs 1 to 21, wherein the step of determining a measure of telomere length includes a step of determining a concentration of the template in the partitions based on the amplification data.

23. The method of any of paragraphs 1 to 22, wherein the step of determining a measure of telomere length includes a step of determining an amount of the genomic DNA present in partitions.

24. The method of paragraph 23, wherein the genomic DNA is provided by a sample, and wherein the amount of the genomic DNA is determined with data for amplification of a reference target in partitions containing at least a portion of the sample.

25. The method of paragraph 24, wherein data for amplification of the template is collected from a first set of partitions, and wherein data for amplification of a reference target is collected from a second set of partitions formed separately from the first set of partitions.

26. The method of paragraph 24, wherein the reference target is present an average of once per genome-equivalent of the genomic DNA.

27. The method of any of paragraphs 23 to 26, wherein the step of determining a measure of telomere length includes a step of determining a ratio based on an amount of the template in partitions and an amount of the genomic DNA in partitions.

28. The method of any of paragraphs 23 to 27, wherein the measure of telomere length is a length value representing an average number of nucleotides or nucleotide base pairs present in intact telomeres of a source that provided genomic DNA for the sample, and wherein the length value is calculated based on a number of copies of the template in partitions and the amount of genomic DNA.

29. The method of paragraph 28, wherein the length value is calculated based on a value from a standard.

30. The method of paragraph 29, wherein the standard has a known average telomere length.

31. The method of any of paragraphs 1 to 30, wherein the measure of telomere length represents a relative length measurement.

32. The method of any of paragraphs 1 to 30, wherein the measure of telomere length represents an absolute length measurement.

33. The method of any of paragraphs 1 to 32, wherein the genomic DNA is a first genomic DNA from a first source, further comprising a step of performing the steps of synthesizing a template, forming partitions, amplifying, and collecting amplification data for a second genomic DNA from a second source, and wherein the step of determining a measure of telomere length for the first genomic DNA is based on data collected for the second genomic DNA from the second source.

34. The method of any of paragraphs 1 to 32, wherein the genomic DNA is provided by a sample, further comprising a step of determining an amount of genomic DNA present in the sample.

35. The method of paragraph 34, wherein the amount of genomic DNA is determined with data collected from partitions containing at least a portion of the sample.

36. The method of paragraph 34, wherein the amount is determined with data collected from partitions formed separately from the partitions containing the template.

37. The method of paragraph 34, wherein an amount of genomic DNA present in the sample is determined in an assay that does not include amplification of nucleic acid.

38. The method of any of paragraphs 1 to 37, wherein the step of determining a measure of telomere length uses a value obtained from at least one standard having a known telomere length.

39. The method of paragraph 38, wherein the value is supplied by a third party.

40. The method of paragraph 38, wherein the value is a factor that allows conversion of (a) an amount of the template synthesized per amount of the genomic DNA to (b) an average length of telomeres present in a source of the genomic DNA.

41. The method of paragraph 38, wherein the value represents a number of copies of the template that are synthesized per unit length of telomere present in the genomic DNA.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of characterizing telomere length, the method comprising:
synthesizing a template with a first primer and a second primer in a bulk phase reaction mixture containing genomic DNA, the template representing a repetitive telomeric sequence present in the genomic DNA and containing a binding site introduced by one of the primers, wherein the one primer includes a 3' portion that binds a repetitive telomeric sequence in the genomic DNA and also includes a 5' portion that is not required for binding to the repetitive telomeric sequence, and wherein the 5' portion of the one primer introduces the binding site;
forming partitions after synthesizing the template in the bulk phase reaction mixture, with only a subset of the partitions containing at least one copy of the template;
amplifying at least a region of the template in partitions to form an amplicon in the presence of a probe that specifically binds to a region of the amplicon that corresponds to the binding site;
collecting amplification data from the probe in partitions; and
determining a measure of telomere length for the genomic DNA based on the amplification data.

2. The method of claim 1, wherein the step of synthesizing a template includes a step of thermally cycling the bulk phase reaction mixture for at least two cycles, and wherein the bulk phase reaction mixture is heated to a denaturation temperature and cooled to an annealing temperature in each cycle.

3. The method of claim 1, wherein the partitions are droplets.

4. The method of claim 1, wherein the amplification data allows determination of a value for a fraction of the partitions that are negative partitions containing no copies of the template.

5. The method of claim 1, wherein the step of determining a measure of telomere length includes a step of determining a concentration of the template in the partitions based on the amplification data.

6. The method of claim 5, wherein the step of determining a measure of telomere length includes (a) a step of determining a number of copies of the template in partitions based on the concentration and (b) a step of determining an amount of the genomic DNA present in partitions.

7. The method of claim 6, wherein the genomic DNA is provided by a sample, and wherein the amount of the genomic DNA is determined with data for amplification of a reference target in partitions containing at least a portion of the sample.

8. The method of claim 1, wherein the step of determining a measure of telomere length includes a step of determining a ratio based on the number of copies of the template and the amount of the genomic DNA.

9. The method of claim 1, wherein the step of determining is based on a value from a standard having a known average telomere length.

10. The method of claim 1, wherein the genomic DNA is a first genomic DNA from a first source, further comprising a step of performing the steps of synthesizing, forming partitions, amplifying, and collecting data for a second genomic DNA from a second source, and wherein the step of determining a measure of telomere length for the first genomic DNA is based on data collected with the second genomic DNA from the second source.

11. The method of claim 1, wherein the genomic DNA is provided by a sample, further comprising a step of determining an amount of genomic DNA present in the sample.

12. The method of claim 1, wherein the template provides a first target, further comprising a step of determining a level of a second target in the genomic DNA based on amplification data collected from the partitions, and wherein the level of the second target indicates a number of genome-equivalents represented by the genomic DNA.

13. The method of claim 1, wherein the step of amplifying is performed with a third primer that is different from the first primer and the second primer.

14. The method of claim 1, wherein the 5' portion of the one primer introduces a binding site for a third primer during template synthesis, and wherein the step of amplifying is performed in the presence of the third primer.

15. The method of claim 14, wherein the step of amplifying generates an amplicon having complementary strands, and wherein the third primer binds specifically to each of the complementary strands.

* * * * *

SEQUENCE LISTING

<160> NUMBER OF SEQ ID NOS: 8

<210> SEQ ID NO 1
<211> LENGTH: 68
<212> TYPE: DNA
<213> ORGANISM: Artificial sequence
<220> FEATURE:
<223> OTHER INFORMATION: primer

<400> SEQUENCE: 1

```
gcggtcccaa aagggtcagt aagagaccca agcaaggttt gggtttgggt ttgggtttgg      60
gttagtgt                                                              68
```

<210> SEQ ID NO 2
<211> LENGTH: 55
<212> TYPE: DNA
<213> ORGANISM: Artificial sequence
<220> FEATURE:
<223> OTHER INFORMATION: primer

<400> SEQUENCE: 2

```
gcggtcccaa aagggtcagt tatccctatc cctatcccta tccctatccc taaca           55
```

<210> SEQ ID NO 3
<211> LENGTH: 20
<212> TYPE: DNA
<213> ORGANISM: Artificial sequence
<220> FEATURE:
<223> OTHER INFORMATION: primer

<400> SEQUENCE: 3

```
gcggtcccaa aagggtcagt                                                  20
```

<210> SEQ ID NO 4
<211> LENGTH: 20
<212> TYPE: DNA
<213> ORGANISM: Artificial sequence
<220> FEATURE:
<223> OTHER INFORMATION: probe

<400> SEQUENCE: 4

```
aaaccttgct tgggtctctt                                                  20
```

<210> SEQ ID NO 5
<211> LENGTH: 53
<212> TYPE: DNA
<213> ORGANISM: Artificial sequence
<220> FEATURE:
<223> OTHER INFORMATION: primer

<400> SEQUENCE: 5

```
gcggtcccaa aagggtcagt ggtttgggtt tgggtttggg tttggggttag tgt            53
```

<210> SEQ ID NO 6
<211> LENGTH: 78
<212> TYPE: DNA
<213> ORGANISM: Homo sapiens

<400> SEQUENCE: 6

```
ccctaaccct aaccctaacc ctaaccctaa ccctaaccct aaccctaacc ctaaccctaa      60
ccctaaccct aaccctaa                                                    78
```

<210> SEQ ID NO 7
<211> LENGTH: 78

```
<212> TYPE: DNA
<213> ORGANISM: Homo sapiens

<400> SEQUENCE: 7
ttagggttag ggttagggtt agggttaggg ttagggttag ggttagggtt agggttaggg        60
ttagggttag ggttaggg                                                     78

<210> SEQ ID NO 8
<211> LENGTH: 109
<212> TYPE: DNA
<213> ORGANISM: Artificial sequence
<220> FEATURE:
<223> OTHER INFORMATION: template strand

<400> SEQUENCE: 8
gcggtcccaa aagggtcagt aagagaccca agcaaggttt gggtttgggt ttgggtttgg        60
gttagtgtta gggttagggt tagggttagg gttagggtta gggttaggg                   109
```